(12) United States Patent
Dijk-van Delden et al.

(10) Patent No.: US 10,233,362 B2
(45) Date of Patent: Mar. 19, 2019

(54) STARCH-CONTAINING ADHESIVE COMPOSITIONS AND USES THEREOF

(71) Applicant: Coöperatie AVEBE U.A., Veendam (NL)

(72) Inventors: Anna Maria Dijk-van Delden, Veendam (NL); Anne Magriet Hofman-de Dreu, Veendam (NL)

(73) Assignee: COOPERATIE AVEBE U.A., Veendam (NL)

( * ) Notice: Subject to any disclaimer, the term of this patent is extended or adjusted under 35 U.S.C. 154(b) by 0 days.

(21) Appl. No.: 15/577,600

(22) PCT Filed: May 27, 2016

(86) PCT No.: PCT/NL2016/050377
§ 371 (c)(1),
(2) Date: Nov. 28, 2017

(87) PCT Pub. No.: WO2016/195486
PCT Pub. Date: Dec. 8, 2016

(65) Prior Publication Data
US 2018/0163098 A1   Jun. 14, 2018

(30) Foreign Application Priority Data

May 29, 2015   (EP) .................... 15169885

(51) Int. Cl.
| | | |
|---|---|---|
| *C09J 103/02* | (2006.01) | |
| *C08K 3/01* | (2018.01) | |
| *C08B 30/12* | (2006.01) | |
| *B32B 7/12* | (2006.01) | |
| *B32B 29/00* | (2006.01) | |
| *B32B 37/12* | (2006.01) | |
| *C09J 5/00* | (2006.01) | |
| *C12P 19/04* | (2006.01) | |
| *C08K 3/34* | (2006.01) | |

(52) U.S. Cl.
CPC ............... *C09J 103/02* (2013.01); *B32B 7/12* (2013.01); *B32B 29/005* (2013.01); *B32B 37/12* (2013.01); *C08B 30/12* (2013.01); *C08K 3/01* (2018.01); *C09J 5/00* (2013.01); *C12P 19/04* (2013.01); *C12Y 204/01018* (2013.01); *C08K 3/346* (2013.01); *C08K 2201/005* (2013.01); *C09J 2400/283* (2013.01); *C09J 2403/00* (2013.01)

(58) Field of Classification Search
CPC ..................................................... C09J 103/02
See application file for complete search history.

(56) References Cited

U.S. PATENT DOCUMENTS

| | | | |
|---|---|---|---|
| 2,380,848 A | 7/1945 | Kerr | |
| 2,772,996 A | 12/1956 | Sams | |
| 2,804,436 A | 8/1957 | Ritson | |
| 2,892,731 A * | 6/1959 | Claxton | ................. C09J 103/02 106/205.7 |
| 2012/0121873 A1 | 5/2012 | Mann et al. | |

FOREIGN PATENT DOCUMENTS

| | | |
|---|---|---|
| EP | 0690170 A1 | 3/1996 |
| EP | 0811719 A1 | 10/1997 |
| EP | 2455436 A1 | 5/2012 |
| WO | 2014003556 A1 | 1/2014 |
| WO | 2014200344 A1 | 12/2014 |

* cited by examiner

*Primary Examiner* — Daniel H Lee
(74) *Attorney, Agent, or Firm* — Hoffmann & Baron, LLP

(57) ABSTRACT

The invention relates to aqueous adhesive compositions comprising a starch, in particular to starch-based adhesives for bonding paper products. Provided is an aqueous adhesive composition comprising a starch derivative and a clay, wherein said starch derivative is a highly branched starch (HBS) obtained by treatment of starch or starch derivatives with a glycogen branching enzyme (EC 2.4.1.18), and wherein the weight ratio of said HBS to said clay is within the range of from about 1:1 to 1:4.

20 Claims, No Drawings

STARCH-CONTAINING ADHESIVE COMPOSITIONS AND USES THEREOF

This application is the U.S. National Phase of, and Applicants claim priority from, International Patent Application Number PCT/NL2016/050377 filed 27 May 2016, which claims priority from EP 15169885.9 filed 29 May 2015, each of which is incorporated herein by reference.

The invention relates to aqueous adhesive compositions comprising a starch, in particular to starch-based adhesives for bonding paper products.

Commercial bonding apparatus for continuously joining paper e.g. to form laminated or corrugated paper board are designed to operate at a high rate of speed, for example, between 175 and 325 feet of paper board per minute. The use of such high speeds greatly limits the choice of adhesives which may be utilized commercially. For example, it will be apparent that the adhesive must have suitable viscosity and other characteristics so that it may be applied to the paper mechanically at a high rate of speed. These characteristics must be readily controllable and relatively stable. Any thickening of the adhesive in the mixing vats or supply tanks, of course, would have serious consequences, possibly resulting in a failure of the process.

At the high rates of speed utilized, it is not feasible to apply considerable pressure to the paper plies during the bonding operation. This is particularly true in the case of corrugated paper board, because of the danger of crushing the corrugations. As a result, poor contact between the plies to be bonded may frequently occur. Accordingly, it is necessary that the adhesive has sufficient viscosity so that it will stand up on the surface of the paper and fill in any areas of poor contact while at the same time wetting the paper sufficiently to form a good bonding zone.

Also, as a direct result of the high rates of speed utilized, the setting of the adhesive must be accomplished in a short period of time. In the space of these few seconds, it is not necessary for the adhesive to become completely dry, but it is essential that a sufficiently strong bond is formed so that the paper board may be immediately cut and handled. In the bonding of corrugated paper board, quick setting is particularly essential to overcome any tendency of the plies to separate due to poor initial contact resulting from the inability to apply pressure during the setting operation.

Starch-based adhesives play a large part in industrial production, especially the packaging industry. Starch and dextrin are principally used for bonding paper products. Most corrugated boxboard for making cartons is bonded with starch-based adhesives, and other porous substrates can be easily joined with these versatile adhesives. Starch-based adhesives are readily available, low in cost, and easy to apply. They are considered to be the least expensive class of paper-packaging adhesive. Formulated starch adhesives can be applied hot or cold. These adhesives are generally supplied as powder and mixed with water prior to use to form a relatively viscous adhesive. Starch-based adhesives cure by the loss of moisture. These adhesives have excellent heat resistance.

Unmodified starches typically come in powder form or as high-viscosity, low-solids content pastes that do not show a stable viscosity with time. Therefore, several treatments have been developed to provide liquid adhesives that are not subject to retrogradation and have a viscosity and rheology more suitable for many applications. These treatment methods include alkali treatment, acid treatment, oxidation and enzyme treatment.

For example, US2012/0121873 (also published as EP2455436-A1) relates to starch-based glue compositions comprising starch obtained by enzymatic modification of starch with a branching enzyme. The branched starch is said to confer a high long-term stability to a glue composition in liquid or aqueous form. Also, the starch-based glue would have a low viscosity and a high adhesive strength.

WO2014/200344 discloses the use of a highly branched starch (HBS) obtained by treatment of starch or starch derivatives with glycogen branching enzyme (EC 2.4.1.18) as binder in combination with a carboxymethylated polysaccharide as rheology-modifying additive in a water-based dispersion adhesive composition. It was found that the combination of the branched starch and a carboxymethylated polysaccharide conferred a number of unexpected desirable functional properties to the adhesive: shear-thinning behaviour, a high dry solids content, a fast setting speed, a high wet tack, a good viscostability (no retrogradation) and low misting/splashing.

Thus, the addition of enzymatically branched starch to aqueous adhesives is known to confer a number of desirable properties. However, the present inventors observed that known glue compositions comprising highly branched starch suffer from the drawback that the setting speed for bonding paper is strongly dependent on the type of paper used. For example, the setting speed for a standard PKL paper was 10 seconds whereas almost twice as long was needed for setting on Reflex special paper. Clearly, such variability in setting speed is undesirable for industrial paper bonding processes since it requires re-adjusting machine settings which is in most cases not possible. Moreover, a slow machine speed is commercially unattractive and it would be highly desirable to run all paper qualities at high machine speed.

One way of increasing the setting speed of industrially used adhesives, e.g. starch based and PVAc/PVOH based adhesives, is to add boron compounds. Because of toxicity concerns, the presence of boron compounds has recently become less desirable, in particular for adhesives which may be used in food contact applications. Starch based adhesives may also contain a significant free amount of a strong base, such as caustic soda, which has become undesirable. These strong bases are aggressive towards many construction materials. Their presence demands for less common construction materials, which adds complexity and investment costs to the process. Strong bases are also aggressive to skin, and therefore demand more complex procedures for the safety of the personnel operating the processes. In some geographies therefore, the use of strong bases, such as used in the high pH streams of the adhesive and cardboard industry, is becoming more and more regulated, and may even one day become prohibited. There is therefore a growing need for adhesive compositions having a lower boron content, preferably being free of boron and/or being about pH neutral or lower.

Accordingly, they set out to overcome this previously unrecognized practical limitations and provide a HBS-based, boron-free adhesive that exhibits excellent tack and setting speed on diverse type of paper and cardboard. Ideally, it is a quick-setting, multi-use water-based adhesive that is suitable as high speed binder, thus having an improved and more versatile industrial performance in paper bonding, including tubewinding, compared to known HBS-based adhesives.

It was surprisingly found that at least some of these goals could be met by including a clay, provided that the weight ratio of HBS to clay is within the range of from about 1:1 to 1:4. Herewith, the setting time of a HBS-based adhesive was much less influenced by the type of paper. More in particular, the setting time of an "HBS only" adhesive for glueing five different types of paper was reduced from 10-19 seconds to only 8.5-12 second upon the addition of clay. Thus, the addition of a clay in the defined weight ratio not only reduces setting time variability but also acts as a setting speed enhancer.

Accordingly, in one embodiment the invention provides an aqueous adhesive composition comprising a starch derivative and a clay, wherein said starch derivative is a highly branched starch (HBS) obtained by treatment of starch or starch derivatives with a glycogen branching enzyme (EC 2.4.1.18), and wherein the weight ratio of said HBS to said clay is within the range of from about 1:1 to 1:4. Also provided is the use of a HBS obtained by treatment of starch or starch derivatives with glycogen branching enzyme (EC 2.4.1.18) in combination with a clay as setting speed enhancer in a water-based dispersion adhesive composition. Preferably, the HBS/clay combination is used in a plasticizer-free adhesive, in particular as alternative for polyvinylacetate (PVAc). The degree of branching can vary and may depend on the intended application.

An adhesive composition of the present invention is not known or suggested in the art. WO2014/200344 in the name of the applicant discloses an aqueous adhesive composition comprising highly branched starch (HBS) obtained by treatment of starch or starch derivatives with a glycogen branching enzyme, and further comprising a carboxymethyl (CM) polysaccharide derivative, such as a carboxymethyl ether of starch, cellulose or a combination thereof. Nothing is mentioned about the use of HBS in combination with clay.

Although mineral fillers, such as kaolin clay, calcium carbonate and titanium dioxide, are often used in starch adhesives to reduce cost and control penetration into porous substrates, they are typically usually used at concentrations of 5-50%. For example, U.S. Pat. No. 2,892,731 relates to adhesives containing kaolin-type clay and adhesive material. Exemplary adhesive materials include polyvinylalcohol, starch or dextrin. The ratio of the kaolin to adhesive material is generally taught to be within the range of form about 1:10 to about 4:1. Notably, U.S. Pat. No. 2,892,731 specifically teaches that in the case of starch corrugating adhesives, about one part to kaolin for each four or five parts of starch material is suitably used. Moreover, U.S. Pat. No. 2,892,731 is completely silent about highly branched starch.

WO2014/003556 in the name of the applicant relates to the field of paper coating. Provided is a method for preparing coated paper comprising the steps of: a) providing a pigmented wet coating formulation comprising water, 2-20 parts of a binder and 100 parts of pigment, wherein at least 50% of the binder is HBS; and wherein at least 70% of the pigment is calcium carbonate; and b) applying the pigmented wet coating formulation to paper by film coating and drying the coated paper. Disclosed in Example 2 is a reference coating composition R2 comprising 100 parts Kaolin pigment (SPS Clay) and 12.5 parts HBS, according to EP0690170B2. The clay is used in more than 10-fold excess by weight over the HBS, which is far outside the currently claimed range.

Example 7 of US2012/0121873 discussed herein above discloses a glue for gluing display cardboard. The glue comprises 20 kg 50% HBS obtained from waxy maize starch and 10 kg of a kaolin suspension (FSG=68%), which corresponds to a HBS:clay ratio of about 1:0.7 by weight. In contrast, an adhesive of the present invention is characterized by at least equal amounts of clay relative to HBS.

As used herein, the term "clay" refers its dictionary definition, i.e. it refers to various forms of hydrated alumino silicate, e.g. those hydrated alumino silicates of general formula $Al_2O_3SiO_2.xH_2O$, where x is the degree of hydration. Commonly known examples of clays include Fuller's Earth, bentonite, kaolin (China clay) and diatomite. Mixtures of two or more clay types are also encompassed, provided that the total amount of clay satisfies the above weight ratio relative to HBS. A preferred clay for use in the present invention is kaolin, for example comprising approximately 45-50% by weight $Al_2O_3$ and approximately 35-45% by weight $SiO_2$.

In one embodiment, the clay comprises or consists of kaolin clay. Kaolin (China clay) is a hydrated aluminium silicate crystalline mineral (kaolinite) formed over many millions of years by the hydrothermal decomposition of granite rocks. Hydrous kaolin is characterized by its fine particle size, plate like or lamellar particle shape and chemical inertness. Kaolin clays, however, are not restricted to a clay composed of the single mineral specie kaolinite, but are represented by at least four distinct species; namely, kaolinite, nacrite, anauxite and dickite, all characterized by the formula above given.

The particle size distribution of the clay can vary according to need. Clays having distinct particle size distributions may also be combined. The particle size distribution is suitably expressed as D-value, which can be thought of as a "mass division diameter". It is the diameter which, when all particles in a sample are arranged in order of ascending mass, divides the sample's mass into specified percentages. For example, the D10 diameter is the diameter at which 10% of a sample's mass is comprised of smaller particles, and the D90 is the diameter at which 90% of a sample's mass is comprised of smaller particles. The D50 is also known as the "mass median diameter" as it divides the sample equally by mass. Preferred clays for use in the present invention have an average particle size of 10 μm or less, more preferably less than 2 μm. Good results were obtained with an adhesive composition comprising clay having a D90 within the range of from about 1 to 20 μm, preferably 1 to 10 μm, more preferably 2 to 5 μm. If desired, the clay may be subjected to a shearing force to reduce aggregate particle size and to improve the uniformity of the particle size distribution, prior to conduct of the present method. The shearing force may be applied, for example, by a mechanical means such as a high-speed mixer or by ultrasound.

The BET surface area of the clay used in the present method is not critical and may typically be from, for example, 5 m2/g to 20 m2/g. Preferred kaolin clays for use in the present method have a BET surface area from 8 m2/g to 16 m2/g.

In a specific aspect, the clay comprises or consists of a kaolin-type clay having a D90 within the range of from about 1 to 20 μm, preferably 1 to 10 μm, more preferably 2 to 5 μm. These clays are commercially available, such as the highly refined kaolin of ultrafine particle size marketed under the tradenames Supreme™ or Speswhite™ by IMERYS Minerals Ltd., UK. Typically, the HBS for use in an adhesive composition has a molecular branching degree of at least 4%, preferably at least 5%. Further additives may be included to enhance product stability. In one embodiment, the HBS has a molecular branching degree of at least 6%. This provides a highly stable product. Preferably, it is at least 6.5%, for example in the range of about 7 to about 10%. The degree of molecular branching as used herein refers to the relative amount of α-1,6 glycosidic linkages over the total of α-1,6 and α-1,4 glycosidic linkages ((α-1,6/(α-1,6+

α-1,4)*100%) and can be determined by methods known in the art, e.g. using a combination of reducing end determination/isoamylolysis (Palomo M et al. 2009 Appl. Environm. Microbiology, 75, 1355-1362; Thiemann, V. et al, 2006 Appl. Microb. and Biotechn. 72: 60-71) and measuring the total amount of carbohydrate present via the Anthrone/sulphuric acid method (see e.g. Fales, F. 1951 J. Biol. Chem. 193: 113-124). Typically, the degree of branching does not exceed 11-12%.

The glycogen branching enzyme (EC 2.4.1.18) can originate from any suitable microbial source. Preferably, it is a thermostable glycogen branching enzyme obtained from a mesophilic or thermophilic organism, preferably glycogen branching enzyme of *Aquifex aeolicus, Anaerobranca gottschalkii* or *Rhodothermus obamensis*. The enzyme may be produced recombinantly using conventional molecular biological and protein expression techniques. The amount of enzyme used depends on the activity of the enzyme source, the starch source and process parameters such as pH and temperature. Typically between 50 and 400 U/g dry weight are employed. One unit (U) is defined as the amount of enzyme that decreases the absorbance at 660 nm of an amylose-iodide complex with 1% per minute. Regarding pH and temperature, the enzymes used in the prior art and in the present invention have a large variety of optimum values. The conversion conditions and the amount of enzyme added vary widely depending on the starting material, the type of enzyme used and desired extent of conversion. The skilled person will be able to determine suitable conditions by routine trial and error. For example, 1000 enzyme units per gram of dry matter starch can yield 10% branching during an incubation period of about 20 hours.

For industrial applications of the enzymatic treatment of starch, it is preferable to use branching enzymes or their mutants that are active at temperatures above 60° C. or higher, or which at least can survive relatively high temperatures. In general, mutations resulting in an increased temperature stability are those that increase the amount of interactions between amino acid residues that are in close vicinity (hydrogen bonds, van der Waals interactions, electrostatic interactions, hydrophobic interactions) or the specific introduction of one or two amino acids containing a sulphur side residue (such as cysteine) that form a sulphur bridge.

Any native or unmodified starch may be used as starting material for obtaining the HBS for use in the present invention. Starch is a natural polymer (a polysaccharide) derived from the seeds, roots and leaves of plants. Only a few plants yield starch in sufficient quantity to be economical: corn, wheat, potato, rice, tapioca and sago. The quality of the starch must be high to produce high-quality adhesives. Starch is made up of two molecules: amylose and amylopectin. Amylose consists of long helical chains, and amylopectin has a branched structure. Its molecular structure and amylase/amylopectin ratio vary according to plant source. Thus, processing characteristics and end properties will vary as well. The most important differences between starches are the molecular weight of the amylose fraction and the ratio of amylose to amylopectin.

For example, the highly branched derivative can be derived from non-GMO as well as GMO plant variants of various sources, such as potato, corn, wheat, tapioca, waxy potato, waxy corn, waxy tapioca, high amylose potato, high amylose corn etc. In one embodiment, HBS is obtained from starch or a starch derivative in a partially or completely gelatinized form, preferably wherein said starch or starch derivative is selected from native, unmodified and chemically modified starch derived from non-genetically modified as well as genetically modified plant variants, such as potato, corn, wheat, tapioca, waxy potato, waxy corn, waxy tapioca, high amylose potato, high amylose corn, and modified starches.

Suitable modified starches include low DE maltodextrins or amylomaltase-treated starch (e.g. Etenia). In one embodiment, the starch derivative is alpha-amylase treated starch. Also encompassed are chemically modified starches. For example, the starting material is a starch derivative selected from the group consisting of the products of acid or enzymatic hydrolysis of starch and the products of the chemical and physical modifications of starch of any type. In a preferred embodiment, the invention provides an adhesive composition comprising HBS obtained from a non-cereal starch, preferably from potato starch.

Preferably, the starch or starch derivative is first gelatinized before it is brought into contact with the branching enzyme. Starch gelatinization is a process that breaks down the intermolecular bonds of starch molecules in the presence of water and heat, allowing the hydrogen bonding sites (the hydroxyl hydrogen and oxygen) to engage more water. This irreversibly dissolves the starch granule. Penetration of water increases randomness in the general granule structure and decreases the number and size of crystalline regions. The gelatinization temperature of starch depends upon botanical source and the amount of water present, pH, types and concentration of salt, sugar, fat and protein in the recipe, as well as derivatisation technology used. Some types of unmodified native starches start swelling at 55° C., other types at 85° C.

For example, starch is gelatinized in a batch or continuous process in a steam injection device (jet cooker). The gelatinized starch can be brought at the desired pH by the addition of acid or base and after the desired temperature has been reached the branching enzyme is added and the solution is kept at the desired temperature for a desired period of time. Alternatively, the branching enzyme can be added to a starch suspension at room temperature and while mixing the slurry is heated to the desired temperature and kept at that temperature for the desired period of time.

After the conversion has progressed to the desired extent, the enzyme can be inactivated by increasing the temperature or by lowering the pH of the incubation mixture. This can then be followed by a filtration and ion exchange step to remove protein. Subsequently, the pH is adjusted to the desired pH and starch mixture is subjected to drying e.g. spray drying or evaporation to remove water and produce a high dry solid mixture.

For example, an adhesive composition of the invention may contain 20-80 wt % dry matter, preferably 25-75 wt % dry matter, more preferably 30-65 wt % dry matter. The amounts of HBS and clay in an adhesive can vary according to specific needs, provided that they are in the defined weight ratio range. Typically, HBS is present in the adhesive composition in an amount of from 5 to 40% (w/w), preferably 10 to 30% (w/w), by weight of the total weight of the composition. The clay content is suitably chosen in an amount of from about 10 to 70% (w/w), preferably 20 to 50% (w/w), by weight of the total weight of the composition. In one specific aspect, the adhesive composition contains 50-65 wt % dry matter, and wherein the weight ratio of HBS to clay is within the range of from about 1:2 to 1:3.

The pH of most conventional aqueous adhesives for paper bonding is slightly acidic, e.g. in the range of about 4-5. It was found that HBS obtained from a non-cereal starch, such as potato starch, tapioca starch, sago or mungbean starch, is advantageously used in an adhesive having a pH below 7. For example, the setting speed of an adhesive based on potato HBS was 8.5 to 11 seconds in the range of pH 3-10 using standard paper, while on paper C the optimum was at pH 4. In contrast, for HBS obtained from waxy maize starch, acceptable setting speeds were observed only at pH 7 or higher.

Accordingly, in one embodiment an adhesive composition of the invention comprises HBS from a non-cereal starch, preferably potato starch HBS, and has a pH below 7, preferably below 6, more preferably within the range of pH 3-5.

The adhesive composition as a whole preferably can combine a favourable performance with regard to avoiding of splashing in paper bonding applications, for which it is theorized that a certain viscosity is needed, with a favourable performance on other aspects that are also such as pump ability and the avoidance of heat build-up due to internal friction as a result of flow. The Brookfield viscosity of an adhesive of the invention is typically within the range of from about 300 to 10000 mPa·s, preferably 500-6000 mPa·s, more preferably 1000 to 5000 mPa·s, wherein the viscosity is measured at a temperature of 25° C. and at 20 rpm. Preferably, the Brookfield viscosity is at most 4400, 4300, 4200, 4100, or even at most 4000 mPa·s.

It is generally held that, while the chemical makeup of starch polymers to make it a good adhesive, its wet tack is too low for many industrial applications. Borax (sodium tetraborate decahydrate) and sodium metaborate (essentially a mixture of borax and sodium hydroxide) dramatically change the properties of starch. Increasing borax content increases viscosity; tack property and cohesiveness are also greatly increased by the addition of borax. It is thought that the addition of borax in the presence of small amounts of sodium hydroxide, changes the starch polymer to a more highly branched chain polymer with higher molecular weight that improves the wet tack. However, in 2009 boric acid, borax and borates were classified as CMR substances (cancerogene, mutagene and toxic for reproduction substances) by the EU for chemical materials with the 30th ATP (Adaptation to Technical Progress). Strictly speaking, borax compounds which are toxic for reproduction category two R 60 and R 61 have to be labeled with a skull. There was a special European ruling that mixtures with less than 5.5% boric acid do not require this strict classification. Within the scope of REACH, however, on 20 Jun. 2011 all boron compounds were classified as SVHC substance (Substances of Very High Concern). This resulted in a stricter classification and it is relevant from a content of 0.1%. Due to its toxic categorisation of reproduction toxicity, borax has become a controversial raw material that the paper and corrugated cardboard industry would like to replace. In particular, there is an urgent need for borax-free adhesives which can be applied to manufacturing papers, paperboards and cardboards in contact with foodstuffs.

The applicants have further found that with the combination of HBS and clay in the defined weight ratio, the addition of a boron compound, such as borax, is not anymore required and may also be dispensed with. The adhesive composition according to the present invention may thus be substantially free of free strong base or free caustic soda, and/or may be substantially free of any boron containing compounds, such as borax. This brings the advantage that the adhesive composition which may be used without raising any of the recent toxicity and/or industrial hygiene concerns associated with boron, borax and/or caustic soda. An adhesive composition according to the invention can thus be labelled as "green" or "environmentally friendly" in the sense that it does not require the presence of any unwanted (synthetic) components such as polyvinylacetate, borates (Borax), and the like, for a good bonding performance. Herewith, it is widely applicable to any paper product including food-related products like pizza-boxes or confectionary packaging, or pharmaceutical, cosmetic or and personal care packaging, like tissue boxes. Accordingly, in one embodiment the adhesive composition is essentially free of non-natural components, in particular PVAc and/or borate, and thus applicable as food contact grade adhesive, i.e. for use in food contact materials which are materials that are intended or expected to be in contact with food.

As will be understood by the person skilled in the art, the adhesive composition according to the invention may further contain conventional admixtures or fillers, additives, salts, buffer components or biocides. Such additives or fillers may be used in particular to finely adjust viscosity, solid content, stability, bond strength, rheology, drying rate, flexibility, water-resistance and fungal-resistance. Furthermore, it is of note that the invention is in no way limited or restricted to "green" adhesives. Any additive, including PVAc, PVOH and/or borate, may be added according to need.

A further aspect of the invention relates to a method for adhering a first substrate to a second substrate, comprising applying to at least said first or said second substrate a water-based adhesive composition according to the invention. Preferably wherein at least one of said substrates is a paper, cardboard, glass or wood substrate. More preferably, both substrates are selected from paper and cardboard. In one embodiment, the method comprises the manufacture of a tube.

In a specific embodiment, said first and/or said second substrate is a paper substrate having at least one of the following properties:

(i) grammage in the range of about 60 to about 250 g/m$^2$
(ii) water absorbance expressed as Cobb30 in the range of 12 to 40 g/m$^2$
(iii) Dennison wax in the range of about Nr. 10 to Nr. 25.

Preferably, the paper substrate has at least two, more preferably all, of the above properties.

The process according to the present invention may further comprise the production of laminated corrugated paper or card board, optionally comprising a plurality of super imposed layers of corrugated paper or card connected together by intermittent flat sheets of paper, whereby an amount of the above described adhesive composition is applied to the top of the corrugations, after which the layers are adhered to each other under pressure.

Also encompassed is a glued product obtainable by adhering a first substrate to a second substrate according to a method of the invention. The article made by the process according to the present invention may be selected from the group consisting of laminated non-corrugated or corrugated paper or card board, cardboard, corrugated cardboard, optionally in the form of a tube or a spiral tube, and a container or packaging container comprising cardboard or corrugated cardboard.

EXPERIMENTAL SECTION

Methods:
Brookfield viscosity
The viscosity of the solution (25±1° C.) is determined with a digital Brookfield DV-I viscosimeter (mPa·s)

using the correct applicable spindle at 20 rpm during 15 seconds (or five revolutions)

Dry solids 1.5 to 2.5 gram of adhesive is applied with a wire winded rod of 200 μm on a predried glass fibre filter for an IR balance (material number: 6909640) and dried with IR of 80° C. to constant mass Refractive index The refractive index is determined with a Bellingham+ Stanley RFM300+Refractometer. at 25±0.1° C.

Adhesion—Setting time

The setting time of the adhesive is determined with a Fipago-Adhesion tester (PKL system) in a conditioned room (RH=50±2%, T=23±1° C.). A thin adhesive film (standard 60 μm) of liquid adhesive (23±1° C.) is applied with a wire winded rod on the smooth side of a standard kraft paper stripe (Natural machine-glazed kraft paper (one smooth and shiny side, one matt side) Manufacterer: Sopal Doetinchem, The Netherlands; Gurley porosity: 72 s; PPS smoothness (smooth side): 3.42 μm; Cobb 60: 24 g/m2; Grammage: 85 g/m2; Dennison wax test: 18; 30×200 mm).

The open time is set on 0 s. The glued paper strip is placed on another piece of paper (kraftliner Pitea Royal Brown, Manufacterer: Kappa Smurfit, Sweden; Supplier: Fipago, The Netherlands (Fipago 2006 kraftline); Grammage: 200 g/m2; Cobb 1800: 86 g/m2; Dennison wax test: 18; 60×100 mm) by means of a metal pressure roller (standard 500 g). After the close time is exceeded (varied in the interval 0 . . . 20 seconds, but can be longer if fibre tear has not yet occurred) the two pieces of paper are separated from each other. Every adhesive is characterized by at least five different closed times, yielding a more or less sigmoid curve. This curve represents the work needed to overcome the bond strength as function of closed time. Results are given as work (cJ). The value for the setting time (s) is the time where the peel strength of 40 cJ is exceeded.

Preparation:

HBS

HBS was produced by jet cooking. A 17% dry solid potato starch slurry was jet cooked (149-153° C., 8 min residence time, pressure 4 bar). After cooling down to 70° C. and adjusting the pH to 6.1, 1000 units of branching enzyme (measured as the change in the absorbance of a iodine/iodide starch complex at 660 nm) were added per gram dry substance of starch. The branching enzyme used was the product NS28067 of Novozymes, a pilot plant product containing the branching enzyme of *Rhodothermus obamensis*.

After 20 h of incubation, the enzyme was inactivated by lowering the pH to 2.5 with 4M HCl. After 35 min the pH was readjusted to 4.5. Then the solution was filtered over a filter with pore size of 2-4 micrometer, followed by ion-exchange (Aquadem E200, Kruger). Finally, the solution was dried by evaporation of the water first at 61° C. and then spray dried at 200° C. (temp out 82° C.). This yielded starch having a degree of branching of 10%.

The activity of the branching enzyme is determined by monitoring changes in the iodine/iodide/amylose complex as a result of the branching enzyme activity. A substrate solution is prepared by adding 10 mg Amylose type III (Sigma) to 0.5 ml 2 M NaOH, subsequently adding 1 ml ultra pure water and then adjusting the pH by adding 0.5 ml 2 M HCl and 7.8 ml phosphate buffer (pH 7.2). An iodine/iodide stock solution is prepared by adding 0.26 g I2 and 2.6 g KI to 10 ml ultra pure water. To 100 microliter of this stock solution, 50 microliter 2 M HCl is added and 26 ml ultra pure water (stop reagent). The activity of the enzyme is determined by mixing 50 microliter of appropriately diluted enzyme to 50 microliter of amylose substrate solution and incubation this for 30 min at 60° C. Then, 2 ml of stop reagent is added and after mixing well the absorbance is measured at 660 nm (the absorbance should be between 0.15 and 0.3).

The activity (U/mL) is calculated using the following formula:

$$U/ml = (OD\text{reference} - OD\text{sample}) \times 100\% \times \text{dilution}/(OD\text{reference} - OD\text{blank})/30\ min/0.05\ ml$$

HBS/clay adhesive

HBS and clay were dry mixed in the appropriate weight ratio until homogenous. The resulting mixture was dissolved by adding the product in about 10 seconds (in a steady flow) to demineralised water (25±1° C.) in a plastic beaker (Ø 90 mm), while being stirred at 1000 rpm with a 3-propeller stirrer (Ø 60 mm) for 30 minutes.

Example 1: Influence Paper Type on Setting Speed of a HBS Adhesive and HBS/Clay Adhesive This example shows the influence of the paper type on the setting speed of a potato starch HBS adhesive and a potato starch HBS/clay adhesive. To rule out the possible effect of viscosity, both adhesives were tested at comparable viscosities.

Potato Starch HBS/Clay Adhesive:
  52.00 gram HBS
  104.00 gram Speswhite (highly refined kaolin of ultrafine particle size from Imerys)
  93.75 gram water Potato Starch HBS Adhesive:
  potato starch HBS is dissolved in a product to water ratio to result in a viscosity of 3000-3500 mPa·s.

The tested paper types are characterized by:

| Name | Grammage [g/m$^2$] | Water absorbance [g/m$^2$] Cobb30 | Cobb60 | Dennison Wax [Nr] | Gurley Porosity [s/100 ml] |
|---|---|---|---|---|---|
| Standard PKL paper | 85 | | 24 | 18 | 72 |

| Name | Grammage [g/m²] | Water absorbance [g/m²] Cobb30 | Cobb60 | Dennison Wax [Nr] | Gurley Porosity [s/100 ml] |
|---|---|---|---|---|---|
| Reflex Special | 70.7 | 15.1 | | 20 | 142 |
| Paper A | 229.6 | 34.3 | | 12 | >1000* |
| Paper B | 72.3 | 13.4 | | 20 | 461 |
| Paper C | 73.1 | 24.2 | | 23 | >1000* |

*too closed surface, could not be measured

| | Experiment | |
|---|---|---|
| | 1 | 2 |
| Adhesive type | HBS/Clay | HBS |
| Properties: | | |
| Brookfield viscosity [mPa · s], 25° C., RVT, 20 rpm Directly after preparation | 3320 | 3250 |

-continued

| | Experiment | |
|---|---|---|
| | 1 | 2 |
| Dry solids [%] | 62.0 | 51.0 |
| pH | 4.2 | 4.2 |
| Standard PKL paper | | |
| Setting time [s] Reflex Special | 8.5 | 10 |
| Setting time [s] Paper A | 9 | 19 |
| Setting time [s] | 12 | 17.5 |

-continued

| | Experiment | |
|---|---|---|
| | 1 | 2 |
| Paper B | | |
| Setting time [s] Paper C | 12 | 15 |
| Setting time [s] | 11.5 | 17 |

Example 1 shows that for the adhesive based solely on HBS the setting speed is strongly dependent on the type of paper adhered. In contrast, the setting speed of the HBS/clay adhesive is almost not influenced by the type of paper adhered. This demonstrates that clay is not only a filler but also a setting speed enhancer.

Example 2: Influence Amount of Clay on Adhesive Properties

This example demonstrates the influence of the weight ratio HBS (potato starch):clay (Speswhite) on adhesive properties. The amount of water used for the preparation of the formulations was such that a viscosity of 2500-4500 mPa·s was obtained.

| | Experiment | | | | | | | | |
|---|---|---|---|---|---|---|---|---|---|
| | 3 | 4 | 1 | 5 | 6 | 7 | 8 | 9 | 10 |
| Weight Ratio HBS:clay Properties: | 1:0 | 1:0.5 | 1:1 | 1:2 | 1:3 | 1:4 | 1:5 | 1:6 | 1:10 |
| Brookfield viscosity [mPa · s], 25° C., RVT, 20 rpm Directly after preparation | 3250 | 2730 | 3320 | 2700 | 3440 | 3310 | 2930 | 4300 | 4210 |
| Dry solids [%] | 51.0 | 57.5 | 62.0 | 60.2 | 62.6 | 62.1 | 61.3 | 63.0 | 61.9 |
| pH | 4.2 | 4.3 | 4.2 | 4.2 | 4.2 | 4.5 | 4.6 | 4.6 | 4.8 |
| Standard PKL paper | | | | | | | | | |
| Setting time [s] Reflex Special | 10 | 10 | 8.5 | 9.5 | 9.5 | 10 | 14 | n.a.* | n.a.* |
| Setting time [s] | 19 | 13 | 9 | 9 | 9.5 | 10 | 14 | n.a.* | n.a.* |

*The dried adhesive film has no internal strength; a force of 40 cJ is not reached Example 2 shows that the ratio of potato starch HBS:clay has an influence on the setting speed on different paper types. If the amount of clay is too low a difference in setting speed between the paper types is observed. On the other hand, if the amount of clay is too high the formulation acts like a coating and not as an adhesive, thus resulting in very poor internal strength. To obtain fast setting at various paper types the ratio of HBS:clay should be between 1:1 and 1:4

Example 3: Adhesive Properties of HBS with Various Types of Clay

Recipe:
 52.00 gram potato starch HBS
 104.00 gram clay
 93.75 gram water

After preparation the products were, if applicable, diluted with water to a viscosity of 3000-5000 mPa·s. Products with a viscosity below 2000 mPa·s were prepared again with a lower amount of water to achieve a viscosity of 2700-3700 mPa·s

| | Experiment | | | | | | |
|---|---|---|---|---|---|---|---|
| | 11 | 1 | 12 | 13 | 14 | 15 | 16 |
| Product | B1 | Speswhite | Argirec B22 | Polwhite B | KKA-HB | KKA-KA | HC |
| Type | Clay | Kaolin | Kaolin | Kaolin | Kaolin | Kaolin | Clay |
| D90 [μm] | 1.0 | 3.0 | 4.5 | 8.6 | 10.1 | 22 | 102 |
| Properties: | | | | | | | |
| Brookfield viscosity [mPa · s], 25° C., RVT, 20 rpm Directly after preparation | 27000 | 3320 | 14500 | 3500 | 3080 | 3530 | 2020 |
| After diluting | 4900 | n.a. | 3470 | n.a. | n.a. | n.a. | n.a. |
| Dry solids [%] | 55.9 | 62.0 | 58.3 | 63.1 | 66.8 | 65.6 | 62.4 |
| pH | 5.4 | 4.2 | 4.0 | 4.2 | 5.6 | 5.6 | 4.3 |
| Standard PKL paper | | | | | | | |
| Setting time [s] | 15 | 8.5 | 12 | 12 | 13 | 15 | >45 |

Example 3 shows that the D90 of the clay has an influence on the setting speed with an optimum at a D90 of around 3 μm. In order to obtain a fast setting, the D90 of the clay is preferably in the range between 1 and 20 μm.

Example 4: Adhesive Properties of HBS from Various Botanical Origins Combined with Clay Recipe:
52.00 gram HBS
104.00 gram Speswhite (highly refined kaolin of ultrafine particle size from Imerys)
93.75 gram water After preparation the products were, if applicable, diluted with water to a viscosity of 3000-5000 mPa·s.

| | Experiment | | | | |
|---|---|---|---|---|---|
| | 1 | 17 | 18 | 19 | 20 |
| Botanical origin HBS | Potato | Waxy Potato | Tapioca | Maize | Waxy Maize |
| Properties: | | | | | |
| Brookfield viscosity [mPa · s], 25° C., RVT, 20 rpm Directly after preparation | 3320 | 1700 | 3000 | 49100 | 48500 |
| After diluting | n.a. | n.a. | n.a. | 4050 | 4740 |
| Dry solids [%] | 62.0 | 61.6 | 61.3 | 40.6 | 40.6 |
| pH | 4.2 | 5.6 | 4.0 | 4.3 | 4.8 |
| Standard PKL paper | | | | | |
| Setting time [s] | 8.5 | 8.5 | 9.0 | 24.5 | 21.0 |

| | Experiment | | | |
|---|---|---|---|---|
| | 21 | 22 | 23 | 24 |
| Botanical origin HBS | Wheat | Pea | Sago | Mungbean |
| Properties: | | | | |
| Brookfield viscosity [mPa · s], 25° C., RVT, 20 rpm Directly after preparation | 49800 | 6840 | 1350 | 1520 |
| After diluting | 3800 | 3500 | n.a. | n.a. |
| Dry solids [%] | 42.1 | 60.3 | 61.5 | 62.2 |
| pH | 4.3 | 3.7 | 3.8 | 3.9 |
| Standard PKL paper | | | | |
| Setting time [s] | 24.5 | 16.5 | 10.5 | 10.5 |

Example 4 surprisingly shows that HBS combined with clay obtained from potato, waxy potato, tapioca, sago or mungbean starch results in a fast setting, shear thinning adhesive in the acidic pH range. In contrast, the use of maize, waxy maize or wheat HBS in combination with clay results in slow setting shear thinning adhesive. Pea HBS combined with clay shows borderline setting speed.

Example 5: Influence pH on Adhesive Properties of an Adhesive with a HBS:Clay Weight Ratio of 1:2

In this example the impact of the pH on the wet tack and setting speed of an adhesive with HBS and clay (1:2 by weight) is shown for HBS originating from potato and waxy maize.

Recipe:
52.00 gram HBS (from potato (P) or waxy maize (WM))
104.00 gram Speswhite
93.75 gram water After preparation the pH is brought to the desired level with either 6N HCl or 25% NaOH. The solutions were, if applicable, diluted with water to a viscosity of 3000-5000 mPa·s.

|  | Experiment | | | | | | | | |
|---|---|---|---|---|---|---|---|---|---|
|  | 25 | 26 | 27 | 28 | 29 | 30 | 31 | 32 | 33 |
| Origin HBS[1] | P | P | P | P | P | WM | WM | WM | WM |
| Properties: | | | | | | | | | |
| Brookfield viscosity [mPa·s], 25° C., RVT, 20 rpm | 3410 | 3320 | 2730 | 3170 | 3120 | 4740 | 3300 | 2130 | 2230 |
| Dry solids [%] | 56.0 | 62.0 | 62.0 | 60.1 | 61.5 | 40.6 | 59.7 | 62.7 | 62.2 |
| pH | 2.8 | 4.2 | 6.9 | 9.0 | 10.6 | 4.8 | 7.0 | 9.0 | 10.4 |
| Standard PKL paper | | | | | | | | | |
| Setting time [s] Paper C | 9 | 8.5 | 9.5 | 10 | 10 | 23.5 | 11 | 9 | 9.5 |
| Setting time [s] | 12.5 | 9.5 | 13 | 13.5 | 12.5 | 30 | 15 | 12 | 12.5 |

[1]P = Potato, WM = Waxy maize

This experiment shows that at pH between 2.8 and 10.6 the adhesive based on potato HBS shows comparable setting speed at standard PKL paper. On Paper C the optimum pH is around 4. For the adhesive based on waxy maize HBS the pH needs to be at least 7, the optimum on both tested paper types is around 9. At pH 9 and higher, potato HBS and waxy maize HBS show comparable wet tack and setting times on both standard PKL paper and Paper C.

Example 6: Influence pH on Adhesive Properties of an Adhesive with a HBS:Clay Weight Ratio of 1:3

In this example the impact of the pH on the wet tack and setting speed of an adhesive with HBS and clay (1:3 by weight) is shown for HBS originating from potato and waxy maize.

Recipe:
  50.0 gram HBS
  150.0 gram Speswhite
  110.0 gram water

After preparation the pH was brought to the desired level with either 6N HCl or 25% NaOH. The solutions were, if applicable, diluted with water to a viscosity of 2200-4000 mPa·s.

|  | Experiment | | | | | | | | |
|---|---|---|---|---|---|---|---|---|---|
|  | 34 | 35 | 36 | 37 | 38 | 39 | 40 | 41 | 42 |
| Origin HBS[1] | P | P | P | P | P | WM | WM | WM | WM |
| Properties: | | | | | | | | | |
| Brookfield viscosity [mPa·s], 25° C., RVT, 20 rpm | 3790 | 3440 | 2690 | 3340 | 3230 | 3470 | 2550 | 1500 | 2510 |
| Dry solids [%] | 58.1 | 62.6 | 62.6 | 62.4 | 63.1 | 35.7 | 63.0 | 65.3 | 62.8 |
| pH | 3.1 | 4.2 | 7.0 | 8.8 | 10.2 | 4.9 | 7.0 | 9.1 | 10.2 |
| Standard PKL paper | | | | | | | | | |
| Setting time [s] Paper C | 11.0 | 9.5 | 10 | 9 | 8.5 | 50 | 10 | 9.5 | 10 |
| Setting time [s] | 12.5 | 10.5 | 13.5 | 12.5 | 12 | >60 | 13.5 | 12 | 12.5 |

[1]P = Potato, WM = Waxy maize

This experiment shows that at pH between 3.1 and 10.2 the adhesive based on potato HBS shows comparable setting speed at standard PKL paper. On Paper C the optimum pH is around 4.

For the adhesive based on waxy maize HBS the pH needs to be at least 7, whereas the optimum on both tested paper types is around 9.

At pH 7 and higher, potato HBS and waxy maize HBS show comparable wet tack and setting times on both standard PKL paper and Paper C.

Example 7: Influence Ratio HBS:Clay at about pH 10.5 on Adhesive Properties

This example demonstrates the influence of the weight ratio potato starch HBS:clay at a pH of about 10.5 on adhesive properties. The amount of water used for the preparation of the formulations was such that a viscosity of 2200-4000 mPa·s was obtained.

|  | Experiment | | | | | | | |
|---|---|---|---|---|---|---|---|---|
|  | 43 | 44 | 29 | 33 | 38 | 42 | 45 | 46 |
| Ratio HBS:Speswhite | 1:1 | 1:1 | 1:2 | 1:2 | 1:3 | 1:3 | 1:4 | 1:4 |
| Origin HBS | P | WM | P | WM | P | WM | P | WM |
| Properties: | | | | | | | | |
| Brookfield viscosity [mPa·s], 25° C., RVT, 20 rpm | 3290 | 2750 | 3120 | 2230 | 3230 | 2510 | 3510 | 2700 |
| Dry solids [%] | 59.5 | 60.7 | 61.5 | 62.2 | 63.1 | 62.8 | 57.1 | 56.8 |
| pH | 10.0 | 10.5 | 10.6 | 10.4 | 10.2 | 10.2 | 10.4 | 10.7 |
| Standard PKL paper | | | | | | | | |
| Setting time [s] Paper C | 11 | 10.5 | 10 | 9.5 | 8.5 | 10 | 11 | 11 |
| Setting time [s] | 13.5 | 12.5 | 12.5 | 12.5 | 12 | 12.5 | 14 | 15 |

[1] P = Potato, WM = Waxy maize

This example shows that at a pH of about 10.5 HBS originating from potato and waxy maize show at each ratio comparable setting speed on both papers.

The invention claimed is:

1. An aqueous adhesive composition comprising a starch derivative and a clay, wherein said starch derivative is a highly branched starch (HBS) obtained by treatment of starch or starch derivatives with a glycogen branching enzyme (EC 2.4.1.18), and wherein the weight ratio of said HBS to the clay in the composition is within the range of from about 1:1 to 1:4.

2. The adhesive composition according to claim 1, wherein said clay is a kaolin-type clay.

3. The adhesive composition according to claim 1, wherein said clay comprises particles and said clay particles have diameters at which 90% of a sample's mass is comprised of particles within the range of from about 1 to 20 μm.

4. The adhesive composition according to claim 1, having a viscosity within the range of from about 300 to 10000 mPa·s, wherein the viscosity is measured at a temperature of 25° C. and at 20 rpm.

5. The adhesive composition according to claim 1, wherein said HBS has a molecular branching degree of at least 6%, wherein the molecular branching degree is defined as the percentage of α-1,6 glycosidic linkages of the total of α-1,6 and α-1,4 glycosidic linkages ((α-1,6/(α-1,6+α-1,4)*100%).

6. The adhesive composition according to claim 1, wherein the HBS has an average molecular weight (Mw) ranging between $0.5*10^5$ g/mol and $1*10^6$ g/mol.

7. The adhesive composition according to claim 1, wherein said HBS is obtained from starch or a starch derivative in a partially or completely gelatinized form.

8. The adhesive composition according to claim 1, wherein said HBS is obtained from a non-cereal starch.

9. The adhesive composition according to claim 1, wherein the pH of said composition is below 7.

10. The adhesive composition according to claim 1, wherein said adhesive composition contains 20-80 wt % dry matter.

11. The adhesive composition according to claim 1, wherein HBS is present in an amount of from 5 to 40% (w/w), by weight of the total weight of the composition and/or wherein the clay content is from about 10 to 60% (w/w), by weight of the total weight of the composition.

12. The adhesive composition according to claim 1, which contains 50-65 wt % dry matter and wherein the weight ratio of HBS to clay is within the range of from about 1:2 to 1:3.

13. The adhesive composition according to claim 1, comprising less than 0.1 wt % of borates.

14. A method for adhering a first substrate to a second substrate, comprising applying to at least said first or said second substrate a water-based adhesive composition according to claim 1.

15. The method according to claim 14, wherein said first or said second substrate is a paper substrate having at least one of the following properties:
   (i) grammage in the range of about 60 to about 250 g/m²;
   (ii) water absorbance expressed as Cobb30 in the range of 12 to 40 g/m²; and
   (iii) Dennison wax in the range of about Nr. 10 to Nr. 25.

16. A glued product obtainable by adhering a first substrate to a second substrate according to the method of claim 14.

17. The adhesive composition according to claim 1, wherein said starch or starch derivative is selected from native, unmodified and chemically modified starch derived from non-genetically modified as well as genetically modified plant variants, and modified starches including low DE maltodextrins and amylomaltase-treated starch.

18. The adhesive composition according to claim 1, wherein said HBS is obtained from a potato starch.

19. The adhesive composition according to claim 1, wherein the pH of said composition is within the range of pH 3-5.

20. The method according to claim 14, wherein at least one of said substrates is a paper or cardboard substrate.

* * * * *